US00RE44330E

(19) United States
(12) Reissued Patent
Hodges et al.

(10) Patent Number: US RE44,330 E
(45) Date of Reissued Patent: Jul. 2, 2013

(54) ELECTROCHEMICAL CELL

(75) Inventors: Alastair M. Hodges, Blackburn South (AU); Thomas W. Beck, North Richmond (AU); Oddvar Johansen, Somerville (AU)

(73) Assignee: LifeScan Inc., Milpitas, CA (US)

(21) Appl. No.: 13/100,999

(22) Filed: May 4, 2011

Related U.S. Patent Documents

Reissue of:
(64) Patent No.: 7,604,722
Issued: Oct. 20, 2009
Appl. No.: 10/624,823
Filed: Jul. 22, 2003

U.S. Applications:
(63) Continuation of application No. 10/035,924, filed on Dec. 21, 2001, now Pat. No. 6,960,289, which is a continuation of application No. 09/618,515, filed on Jul. 18, 2000, now Pat. No. 6,413,410, which is a continuation of application No. 08/981,385, filed as application No. PCT/AU96/00365 on Jun. 19, 1996, now Pat. No. 6,284,125.

(30) Foreign Application Priority Data

Jun. 19, 1995 (AU) ..... PN3639

(51) Int. Cl.
*G01N 27/327* (2006.01)

(52) U.S. Cl.
USPC ..... 204/403.02; 204/403.04

(58) Field of Classification Search
USPC ..... 204/403.01–403.15; 422/82.01–82.03
See application file for complete search history.

(56) References Cited

U.S. PATENT DOCUMENTS

| | | | |
|---|---|---|---|
| 4,053,381 | A | 10/1977 | Hamblen et al. |
| 4,076,596 | A | 2/1978 | Connery et al. |
| 4,088,448 | A | 5/1978 | Lilja et al. |
| 4,224,125 | A | 9/1980 | Nakamura et al. |
| 4,233,029 | A | 11/1980 | Columbus |
| 4,254,083 | A | 3/1981 | Columbus |
| 4,254,546 | A | 3/1981 | Ullery, Jr. |
| 4,259,165 | A | 3/1981 | Miyake |

(Continued)

FOREIGN PATENT DOCUMENTS

| | | |
|---|---|---|
| AU | 5487394 | 2/1993 |
| AU | 3104293 | 7/1993 |

(Continued)

OTHER PUBLICATIONS

JPO computer generated English language translation of Japanese Patent Applciation Publication 2001-281219, downloaded on Feb. 28, 2011.

(Continued)

*Primary Examiner* — Alex Noguerola
(74) *Attorney, Agent, or Firm* — Hiscock & Barclay LLP

(57) ABSTRACT

This invention relates to a biosensor and more particularly to an electrochemical biosensor for determining the concentration of an analyte in a carrier. The invention is particularly useful for determining the concentration of glucose in blood and is described herein with reference to that use but it should be understood that the invention is applicable to other analytic determinations.

11 Claims, 5 Drawing Sheets

U.S. PATENT DOCUMENTS

| | | | |
|---|---|---|---|
| 4,301,412 | A | 11/1981 | Hill et al. |
| 4,301,414 | A | 11/1981 | Hill et al. |
| 4,303,887 | A | 12/1981 | Hill et al. |
| 4,307,188 | A | 12/1981 | White |
| 4,319,969 | A | 3/1982 | Oda et al. |
| 4,374,013 | A | 2/1983 | Enfors |
| 4,404,065 | A | 9/1983 | Matson |
| 4,404,066 | A | 9/1983 | Johnson |
| 4,431,004 | A | 2/1984 | Bessman et al. |
| 4,431,507 | A | 2/1984 | Nankai et al. |
| 4,508,613 | A | 4/1985 | Busta et al. |
| 4,511,659 | A | 4/1985 | Matson |
| 4,517,287 | A | 5/1985 | Scheibe et al. |
| 4,517,291 | A | 5/1985 | Seago |
| 4,533,440 | A | 8/1985 | Kim |
| 4,545,382 | A | 10/1985 | Higgins et al. |
| 4,552,840 | A | 11/1985 | Riffer |
| 4,554,064 | A | 11/1985 | McClintock et al. |
| 4,591,550 | A | 5/1986 | Hafeman et al. |
| 4,629,563 | A | 12/1986 | Wrasidlo |
| 4,654,197 | A | 3/1987 | Lilja et al. |
| 4,664,119 | A | 5/1987 | Bessman et al. |
| 4,711,245 | A | 12/1987 | Higgins et al. |
| 4,774,039 | A | 9/1988 | Wrasidlo |
| 4,782,265 | A | 11/1988 | Schaper et al. |
| 4,790,925 | A | 12/1988 | Miller et al. |
| 4,897,173 | A | 1/1990 | Nankai et al. |
| 4,900,424 | A | 2/1990 | Birth et al. |
| 4,911,794 | A | 3/1990 | Parce et al. |
| 4,919,770 | A | 4/1990 | Preidel et al. |
| 4,963,815 | A | 10/1990 | Hafeman |
| 4,988,429 | A | 1/1991 | Matthiessen et al. |
| 4,989,452 | A | 2/1991 | Toon et al. |
| 5,059,908 | A | 10/1991 | Mina |
| 5,064,516 | A | 11/1991 | Rupich |
| 5,089,112 | A | 2/1992 | Skotheim et al. |
| 5,089,320 | A | 2/1992 | Straus et al. |
| 5,095,407 | A | 3/1992 | Kanezawa et al. |
| 5,108,564 | A | 4/1992 | Szuminsky et al. |
| 5,120,420 | A | 6/1992 | Nankai et al. |
| 5,122,244 | A | 6/1992 | Hoenes et al. |
| 5,126,034 | A | 6/1992 | Carter et al. |
| 5,128,015 | A | 7/1992 | Szuminsky et al. |
| 5,141,868 | A | 8/1992 | Shanks et al. |
| 5,151,166 | A | 9/1992 | Harral et al. |
| 5,156,972 | A | 10/1992 | Issachar et al. |
| 5,171,689 | A | 12/1992 | Kawaguri et al. |
| 5,192,415 | A | 3/1993 | Yoshioka et al. |
| 5,194,133 | A | 3/1993 | Clark et al. |
| 5,229,282 | A | 7/1993 | Yoshioka et al. |
| 5,243,516 | A | 9/1993 | White |
| 5,243,526 | A | 9/1993 | Ito et al. |
| 5,269,903 | A | 12/1993 | Ikariyama et al. |
| 5,272,087 | A | 12/1993 | El Murr et al. |
| 5,282,950 | A | 2/1994 | Dietze et al. |
| 5,288,636 | A | 2/1994 | Pollmann et al. |
| 5,312,590 | A | 5/1994 | Gunasingham |
| 5,314,605 | A | 5/1994 | Matthiessen et al. |
| 5,320,732 | A | 6/1994 | Nankai et al. |
| 5,354,447 | A | 10/1994 | Uenoyama et al. |
| 5,366,609 | A | 11/1994 | White et al. |
| 5,382,346 | A | 1/1995 | Uenoyama et al. |
| 5,384,028 | A | 1/1995 | Ito |
| 5,385,846 | A | 1/1995 | Kuhn et al. |
| 5,388,163 | A | 2/1995 | Elko et al. |
| 5,393,399 | A | 2/1995 | Van den Berg et al. |
| 5,395,504 | A | 3/1995 | Saurer et al. |
| 5,399,256 | A | 3/1995 | Bohs et al. |
| 5,405,511 | A | 4/1995 | White et al. |
| 5,413,690 | A | 5/1995 | Kost et al. |
| 5,437,999 | A | 8/1995 | Diebold et al. |
| 5,443,710 | A | 8/1995 | Broderick |
| 5,496,453 | A | 3/1996 | Uenoyama et al. |
| 5,508,171 | A | 4/1996 | Walling et al. |
| 5,509,410 | A | 4/1996 | Hill et al. |
| 5,512,159 | A | 4/1996 | Yoshioka et al. |
| 5,517,313 | A | 5/1996 | Colvin, Jr. |
| 5,518,590 | A | 5/1996 | Fang |
| 5,520,787 | A | 5/1996 | Hanagan et al. |
| 5,527,446 | A | 6/1996 | Kosek et al. |
| 5,567,302 | A | 10/1996 | Song et al. |
| 5,575,895 | A | 11/1996 | Ikeda et al. |
| 5,607,565 | A | 3/1997 | Azarnia et al. |
| 5,611,908 | A | 3/1997 | Matthiessen et al. |
| 5,620,579 | A | 4/1997 | Genshaw et al. |
| 5,628,890 | A | 5/1997 | Carter et al. |
| 5,645,709 | A | 7/1997 | Birch et al. |
| 5,651,869 | A | 7/1997 | Yoshioka et al. |
| 5,682,884 | A | 11/1997 | Hill et al. |
| 5,695,947 | A | 12/1997 | Guo et al. |
| 5,707,502 | A | 1/1998 | McCaffrey et al. |
| 5,726,565 | A | 3/1998 | Uchiyama et al. |
| 5,727,548 | A | 3/1998 | Hill et al. |
| 5,762,770 | A | 6/1998 | Pritchard et al. |
| 5,849,174 | A | 12/1998 | Sanghera et al. |
| 5,858,188 | A | 1/1999 | Soane et al. |
| 5,863,400 | A | 1/1999 | Drummond et al. |
| 5,909,114 | A | 6/1999 | Uchiyama et al. |
| 5,942,102 | A | 8/1999 | Hodges et al. |
| 5,997,817 | A | 12/1999 | Crismore et al. |
| 6,071,391 | A | 6/2000 | Gotoh et al. |
| 6,117,289 | A | 9/2000 | Yamamoto et al. |
| 6,153,069 | A | 11/2000 | Pottgen et al. |
| 6,174,420 | B1 | 1/2001 | Hodges et al. |
| 6,179,979 | B1 | 1/2001 | Hodges et al. |
| 6,193,873 | B1 | 2/2001 | Ohara et al. |
| 6,214,205 | B1 | 4/2001 | Willner et al. |
| 6,218,134 | B1 | 4/2001 | Yamauchi et al. |
| 6,251,260 | B1 | 6/2001 | Heller et al. |
| 6,270,637 | B1 | 8/2001 | Crismore et al. |
| 6,284,125 | B1 | 9/2001 | Hodges et al. |
| 6,325,973 | B1 | 12/2001 | Leland et al. |
| 6,413,395 | B1 | 7/2002 | Bhullar et al. |
| 6,413,410 | B1 | 7/2002 | Hodges et al. |
| 6,461,496 | B1 | 10/2002 | Feldman et al. |
| 6,503,381 | B1 | 1/2003 | Gotoh et al. |
| 6,521,110 | B1 | 2/2003 | Hodges et al. |
| 6,544,212 | B2 | 4/2003 | Galley et al. |
| 6,780,756 | B1 | 8/2004 | Farber et al. |
| 6,863,801 | B2 | 3/2005 | Hodges et al. |
| 7,604,722 | B2 | 10/2009 | Hodges et al. |
| 7,608,175 | B2 | 10/2009 | Hodges et al. |
| 2002/0012943 | A1 | 1/2002 | Fowlkes et al. |

FOREIGN PATENT DOCUMENTS

| | | | |
|---|---|---|---|
| AU | 3104293 | A | 7/1993 |
| AU | 5487394 | A | 8/1994 |
| CN | 1325908 | A | 12/2001 |
| CN | 1325908 | | 5/2009 |
| DE | 31 03 464 | A1 | 8/1982 |
| DE | 3103464 | | 8/1982 |
| DE | 3103484 | A1 | 8/1982 |
| DE | 29709141 | | 8/1997 |
| EP | 0125137 | A2 | 11/1984 |
| EP | 0 251 915 | A2 | 1/1988 |
| EP | 0 255 291 | A1 | 2/1988 |
| EP | 0 266 204 | A2 | 4/1988 |
| EP | 0 278 647 | A2 | 8/1988 |
| EP | 0290770 | A2 | 11/1988 |
| EP | 0290770 | B1 | 11/1988 |
| EP | 0299779 | A2 | 1/1989 |
| EP | 0 351 516 | A2 | 1/1990 |
| EP | 0 351 891 | | 1/1990 |
| EP | 0351516 | A2 | 1/1990 |
| EP | 0351891 | A2 | 1/1990 |
| EP | 0351892 | A2 | 1/1990 |
| EP | 0 359 831 | | 3/1990 |
| EP | 0359831 | A1 | 3/1990 |
| EP | 0 171 375 | A1 | 5/1990 |
| EP | 0 367 432 | | 5/1990 |
| EP | 0170 375 | | 5/1990 |
| EP | 0367432 | A1 | 5/1990 |
| EP | 0400918 | | 12/1990 |
| EP | 0400918 | A1 | 12/1990 |
| EP | 0406304 | A1 | 1/1991 |
| EP | 0418404 | A1 | 3/1991 |
| EP | 0 422 708 | | 4/1991 |

| | | | |
|---|---|---|---|
| EP | 0451981 | A2 | 10/1991 |
| EP | 0 127 958 | B2 | 3/1992 |
| EP | 0560336 | A1 | 9/1993 |
| EP | 0 585 933 | | 3/1994 |
| EP | 593096 | A2 | 4/1994 |
| EP | 0 603 954 | | 6/1994 |
| EP | 0603954 | A | 6/1994 |
| EP | 0609760 | A1 | 8/1994 |
| EP | 0735303 | A1 | 10/1996 |
| EP | 0741186 | | 11/1996 |
| EP | 0764469 | | 3/1997 |
| EP | 0 406 304 | B1 | 8/1997 |
| EP | 0964059 | | 12/1999 |
| EP | 0 585 933 | | 12/2005 |
| GB | 2020424 | A | 11/1979 |
| GB | 2154735 | A | 9/1985 |
| GB | 2194112 | | 2/1988 |
| GB | 2201248 | A | 8/1988 |
| GB | 2215846 | | 9/1989 |
| GB | 2215846 | A | 9/1989 |
| GB | 2235050 | A | 2/1991 |
| JP | 6222874 | | 10/1967 |
| JP | 54006595 | | 1/1979 |
| JP | 59003345 | A | 1/1984 |
| JP | 60017344 | | 1/1985 |
| JP | 60244853 | | 12/1985 |
| JP | 60250246 | | 12/1985 |
| JP | 61002060 | | 1/1986 |
| JP | 62228274 | | 10/1987 |
| JP | 63139246 | | 6/1988 |
| JP | 63317097 | A | 12/1988 |
| JP | 01253648 | | 10/1989 |
| JP | 1253648 | A | 10/1989 |
| JP | 1294453 | | 11/1989 |
| JP | 3107747 | A | 5/1991 |
| JP | 3167464 | | 7/1991 |
| JP | 3167464 | A | 7/1991 |
| JP | 4062463 | A | 2/1992 |
| JP | 466112 | A | 3/1992 |
| JP | 4066112 | | 3/1992 |
| JP | 4-343065 | | 11/1992 |
| JP | 4340453 | A | 11/1992 |
| JP | 04343065 | | 11/1992 |
| JP | 04343065 | A | 11/1992 |
| JP | 5-2007 | | 1/1993 |
| JP | 05002007 | | 1/1993 |
| JP | 5002007 | A | 1/1993 |
| JP | 0580018 | | 3/1993 |
| JP | 5080018 | | 3/1993 |
| JP | 5256812 | A | 10/1993 |
| JP | 05-312761 | | 11/1993 |
| JP | 5312760 | A | 11/1993 |
| JP | 5312761 | A | 11/1993 |
| JP | 6150262 | A | 5/1994 |
| JP | 6222874 | | 8/1994 |
| JP | 6224140 | A | 8/1994 |
| JP | 6310746 | | 11/1994 |
| JP | 2 046 361 | C1 | 10/1995 |
| JP | 8062179 | A | 3/1996 |
| JP | 8304340 | | 11/1996 |
| JP | 9222408 | | 8/1997 |
| JP | 9236570 | | 9/1997 |
| JP | 9243588 | | 9/1997 |
| JP | 2001281219 | A | 10/2001 |
| JP | 2007225619 | | 9/2007 |
| RU | 2 043 361 | C1 | 10/1995 |
| SU | 1351627 | A | 11/1987 |
| SU | 1351627 | A2 | 11/1987 |
| SU | 1806187 | | 3/1993 |
| WO | WO89/08713 | | 9/1989 |
| WO | WO-8908713 | A1 | 9/1989 |
| WO | 9005910 | | 5/1990 |
| WO | WO-9005910 | A1 | 5/1990 |
| WO | 9109139 | | 6/1991 |
| WO | WO-9109139 | A1 | 6/1991 |
| WO | WO92/15701 | | 9/1992 |
| WO | WO-9215701 | A1 | 9/1992 |
| WO | WO94/02842 | | 2/1994 |
| WO | WO-9402842 | A1 | 2/1994 |
| WO | WO94/29731 | | 12/1994 |
| WO | WO-9429731 | A1 | 12/1994 |
| WO | WO95/16198 | | 6/1995 |
| WO | WO-9516198 | A1 | 6/1995 |
| WO | WO-9521934 | | 8/1995 |
| WO | WO-9528634 | A1 | 10/1995 |
| WO | WO97/00441 | | 1/1997 |
| WO | WO-9700441 | A1 | 1/1997 |
| WO | 9718464 | | 5/1997 |
| WO | 9718465 | | 5/1997 |
| WO | WO-97/18464 | A1 | 5/1997 |
| WO | WO-9718465 | A1 | 5/1997 |
| WO | WO-9811426 | | 3/1998 |
| WO | 9843074 | | 10/1998 |
| WO | WO-98/43073 | | 10/1998 |
| WO | WO-98/43074 | A1 | 10/1998 |
| WO | WO-9946585 | | 9/1999 |
| WO | 0020626 | | 4/2000 |
| WO | WO-0020626 | A1 | 4/2000 |
| WO | WO-0208763 | | 1/2002 |

OTHER PUBLICATIONS

Patent family history and equivalent filing s for WO 97/00441 A1 downloaded from Derwent on Mar. 4, 2011.

Japanese Office Action Application No. 102675/2007 dated Jan. 8, 2010.

Japanese Office Action for Japanese Application No. 2003-535271 dated Jul. 28, 2010 (3 pages).

Daruhazi, et al., "Cyclic Voltammetry for Reversible Redox-Electrode Reaction in Thin Layer Cells with Closely Separated Working and Auxiliary Electrodes of the Same Size", in J. Electroanal. Chem. 264; 77-89 (1989).

Denuault, et al., Direct Determination of Diffusion-Coefficients by Chronoamperometry at Microdisk Electrodes, Journal of Electroanalytical Chemistry, vol. 308, No. 1-2, 1991, pp. 27-38.

European Search Report for App. No. 99 20 2305, date unknown.

European Search Report for App. No. 03 00 7604 dated May 19, 2003.

Hall, E., Biosensors, Chapter 5: "Amperometric Assay Techniques", 1990.

International Search Report PCT/US02/31289 dated Jul. 18, 2003.

Niwa, et al., Electrochemical Behavior of Reversibel Redox Species at Interdigitated Array Electrodes with Different Geometries: Consideration of Redox Cycling and Collection Efficiency, Analytical Chemistry; Mar. 1990, vol. 62, No. 5, pp. 447-452.

Niwa, et al., Highly Selective electrochemical Detection of Dopamine Using Interdigitated Array of Electrodes Modified with Nafion/Polyester Ionomer Layered Film, Electroanalysis, Vol, 6, No. 3, Mar. 1994, pp. 237-243, XP000943528.

Salbeck, J., Spectrochemical Thin-Layer Cell for Nonaqueous Solvent Systems, Anal. Chem., 1993, vol. 65, pp. 2165-2173.

Seddon, et al., Preparation and Ameprometric Response of Carbon and Platinum Dual Cylinder Microelectrodes, *Electrochimica Acta,* vol. 40, No. 4, Mar. 1, 1995, pp. 455-465.

Trojanek, et al., Data processing in reaction rate measurements, Collect. Chzech. Chem commun., 38(9):2572-2580, 1973.

Uchiyama, et al., Measurement Of Homogeneous Reaction Rate by Concentration-Step, Controlled Potential Electrolysis, J. Electroanal. Chem Interfacial Electrochem., 91(3):301-308, 1978.

Yaoita, et al., Pulse Chronoamperometric Technique of Enzyme Embodied Electrode Applied to Glucose Measurement in Whole Serum, Extended Abstracts, US, Electrochemical Society, Princeton, NJ; vol. 93/1, 1993, p. 2801.

"Enthone—Imaging Technologies Update" Jun. 2001/No. 3).*

European Search Report No. EP 03 00 7604 dated May 19, 2003.

Osamu, Niwa et la., "Electrochemical Behavior of Reversible Redox Species at Interdigitated Array Electrodes with different Geometries: Consideration of Redox Cycling and Collection Efficiency", Analytical Chemistry; Mar. 1990, vol. 62, No. 5, pp. 447-452.

Patent Abstracts of Japan, JP A 04-62463.

Patent Abstracts of Japan, JP A 59-3345, p. 269, p. 166 (Hitachi Seisakusho K.K.) Jan. 10, 1994.

Hubbard, et al. The Theory and Practice of Electrochemistry with Thin Layer Cells, in *Electroanalytical Chemistry,* (Bard, Ed.), Marcel Deletier, New York, 1970, vol. 4 (pp. 129-214).
Japanese Patent Abstract JP63-139246 A2 (Jun. 1988).
Patent Abstracts of Japan, JP 0 05312761 A2; 1993; Y. Fukuda, et al.
Cassidy, et al.; "Novel Electrochemical Device for the Detection of Cholesterol or Glucose"; Analyst, vol. 118; Apr. 1993; pp. 415-418.
Christensen & Anson: "*Chronopotentiometry in Thin Layers of Solution",* Analytical Chemistry, vol. 35; No. 2, 1963, pp. 205-209.
Hubbard & Anson: "*New Electrodes for Chronopotentiometry in Thin Layers of Solution"*, Analytical Chemistry, vol. 36; No. 4, Apr. 1964, pp. 723-728.
McDuffie, Anderson, & Reilley, "*Twin Electrode Thin-Layer Electrochemistry"*, Analytical Chemistry; vol. 38, No. 7, Jun. 1966; pp. 883-890.
Nicholson and Shain: "*Theory of Stationary Electrode Polarography"*, Analytical Chemistry: vol. 36, No. 4, Apr. 1964, pp. 706-723.
Pickup, Kutner, Leidner, and Murray; *Redox Conduction in Single and Bilayer Films of Redox Polymer;* J. Amer. Chem. Soc.; vol. 106; No. 7; 1984.
Chidsey, Feldman, Lundgren, and Murray; "*Micrometer-Spaced Platinum Interdigitated Array Electrod: Fabrication, Theory, and Initial User"*; Analytical Chemistry, vol. 58, No. 3, Mar. 1986, pp. 801-807.
Anderson, McDuffie and Reilley; "*Diagnostic Criteria for the Study of Chemical and Physical Processes by Twin-Electrode Thin-Layer Electrochemistry"*; J. Electroanalytical Chemistry; vol. 12, 1966, pp. 477-494.
Hubbard; "*Study of the Kinetics of Electrochemical Reactions by Thin-Layer Voltammetry"*; J. Electroanalytical Chemistry, vol. 22, 1969, pp. 165-174.
Anderson and Reilley; "*Thin-Layer Electrochemistry:* Steady-State Methods of Studying Rate Process", J. Electroanalytical Chemistry; vol. 10, 1965, pp. 295-305.
Patent Abstracts of Japan, JP 08062179A; *Electrolyte Analyzer;* (Mar. 8, 1996).
Reilley, Charles; "*Electrochemistry Using Thin-Layer Cells"*, Review of Pure and Appl. Chem, vol. 18, 1968, pp. 137-151.
Morris, Franta and White; "*Electrochemistry at Pt Band Electrodes of Width Approaching Molecular Dimensions. Breakdown of Transport Equations At Very Small Electrodes"*, J. Of Physical Chemistry, vol. 91, No. 13, 19874.pp. 3559-3564.
Jung and Kwak; "Simultaneous Determination of Diffusion Coefficient and Concentration by Chronoamperometry at a Microdisk Electrode";*Bull Korean Chem. Soc.;* 1004, v. 15, No. 3, pp. 209-213 1994.
Specification sheet from Adhesives Research, Inc., ARCIad®8314 (May 2, 1997) (1 pg.).
Specification sheet from Adhesives Research, Inc., ARCare®7148, double-sided adhesive coated polyster film (Mar. 30, 1995) (2 pages).
Oglesby, Omang, and Reilley; "*Thin Layer Electrochemical Studies Using Controlled Potential or Controlled Current"*, Analytical Chemistry, vol. 37, No. 11, Oct. 1965, pp. 1312-1316.
European Search Report for App. No. 96 93 7919.
European Search Report for App. No. 99 20 2305.
O. Niwa, M. Morita, H. Tabei, "Highly Selective Electrochemical Detection of Dopamine Using Interdigitated Array of Electrodes Modified with Nafron (sp?) Polyester Ionomer Layered Film", Electroanalyis, vol. 6, No. 3, Mar. 1994, pp. 237-243, XP000943528.
Paeschke, et al., "Dynamic Redox Recycling of Cytochrome C", Journal of Electroanalytical Chemistry; vol. 393, No. 1/02, 1995, pp. 131-135.
Paeschke, et al., Properties of Interdigital Electrode Arrays With Different Geometries, Analytical Chimica Acta; vol. 305, No. 1/03, 1995, pp. 126-136.
Salbeck, J., Spectrochennical Thin-Layer Cell for Nonaqueous Solvent Systems, Anal. Chem., 1993, vol. 65, pp. 2165-2173.
Seddon, et al., Preparation and Amperometric Response of Carbon and Platinum Dual Cylinder Microelectrodes, Electrochimica Acta, vol. 40, No. 4, Mar. 1, 1995, pp. 455-465.
Trojanek, et al., Data processing in reaction rate measurements, Collect, Chzech. Chem commun., 38(9):2572-2580, 1973.
Vidal, J.C. et al., "A Chronoamperometric Sensor for Hydrogen Peroxide Based on Electron Transfer Between Immobilized Horseradish Peroxidase on a Glassy Carbon Electrode and a Diffusing Ferrocene Mediator", Sensors and Actuators B:Chemical, vol. 21, Issue 2, Aug. 1994, pp. 135-141.
Chinese Office Action (Application No. CN200610100717.9) dated Dec. 5, 2008.

* cited by examiner

ELECTROCHEMICAL CELL

Matter enclosed in heavy brackets [ ] appears in the original patent but forms no part of this reissue specification; matter printed in italics indicates the additions made by reissue.

This is a continuation of application Ser. No. 10/035,924, filed Dec. 21, 2001, now U.S. Pat. No. 6,960,289 which is a continuation of application Ser. No. 09/618,515, filed Jul. 18, 2000, now U.S. Pat. No. 6,413,410, which is a continuation of application Ser. No. 08/981,385, filed Apr. 17, 1998, now U.S. Pat. No. 6,284,125, which is the national phase under 35 U.S.C. §371 of PCT International Application No. PCT/AU96/003 65, which has an International filing date of Jun. 19, 1996, which designated the United States of America, which was published by the International Bureau in English on Jan. 3, 1997, and which claims priority to Australian Provisional Application No. PN 3639, filed Jun. 19, 1995.

FIELD OF THE INVENTION

This invention relates to a biosensor and more particularly to an electrochemical biosensor for determining the concentration of an analyte in a carrier. The invention is particularly useful for determining the concentration of glucose in blood and is described herein with reference to that use but it should be understood that the invention is applicable to other analytic determinations.

BACKGROUND OF THE INVENTION

Electrochemical biosensors generally comprise a cell having a working electrode, a counter electrode and a reference electrode. Sometimes the function of the counter and reference electrodes are combined in a single electrode called a "counter/reference" electrode or "pseudo reference electrode". As herein used the term "counter electrode" includes a counter/reference electrode where the context so admits.

The sample containing the analyte is brought into contact with a reagent containing an enzyme and a redox mediator in the cell. Either the mediator is reduced (receives at least one electron) while the analyte is oxidised (donates at least one electron) or visa versa. Usually it is the analyte which is oxidised and the mediator which is reduced. The invention will be herein described principally with reference to that system but it is also applicable to systems in which the analyte is reduced and the mediator oxidised.

Electrochemical glucose analysers such as those used by diabetics to monitor blood glucose levels or such as are used in clinics and hospitals are commonly based upon the use of an enzyme such as glucose oxidase dehydrogenase (GOD) and a redox mediator such as a ferricyanide or ferrocyanide. In such prior art system, the sample (e.g. blood) containing the analyte (e.g. glucose) is brought into contact with the reagents in the cell. Glucose is oxidised to gluconic acid and the glucose oxidase is thereby reduced. The mediator then re-oxidizes the glucose oxidase and is reduced in the process. The reduced mediator is then re-oxidized when it transfers electrons to the working electrode. After allowing passage of a predetermined time, sufficient to obtain an accurate estimate of the Faraday current, the concentration of glucose is estimated from the magnitude of the current or voltage signal then measured.

Prior art electrochemical cells consist of two (or three) adjacent electrodes spaced apart on one side of an insulator and adapted for connection to a measuring device. A target area on which the blood sample is placed is defined on or between the electrodes. Co-pending Application PCT/AU95/00207 describes a cell in which electrodes are: disposed on opposite sides of a porous membrane, one of the electrodes having a liquid permeable target area.

In the prior art there is a need to separate the working electrode from the counter (or counter/reference) electrode by a sufficient distance to avoid products of electrochemical reaction at one electrode from interfering with those at the other. In practice a separation of the electrodes of more than 500 μm is required to achieve acceptable accuracy.

Each batch of cells is required to have been previously calibrated and leads to inaccuracies during use because of variations within the batch, in sample composition and in ambient conditions.

It is desired to improve, the accuracy and reliability of such biosensors. Achievement of these objectives is made difficult in the case of sensors intended to determine the concentration of analytes in blood because blood contains dissolved gases, ions, colloids, complex micelles, small scale cellular debris, and living cellular components in a predominantly aqueous medium. Any of these may interfere in the determination. Existing sensors are also susceptible to influence from other interfering substances that may be present in the sample and which may be oxidised at the working electrode and mistakenly identified as the analyte of interest. Alternatively, the interfering substances may reduce the oxidised form of the redox mediator. These effects will give artificially elevated estimates of the analyte concentration. Additionally there is always some reduced redox mediator present before the analyte is added and its concentration needs to be known and subtracted from the measured value of reduced mediator to give an accurate concentration of the analyte. Moreover, oxygen in the blood may act as a redox mediator for glucose oxidase dehydrogenase (GOD) in competition with ferrocyanide. Thus high oxygen concentrations can lead to low estimates of glucose concentration. In addition the measurements are sensitive to factors such as changes in humidity, temperature, solution viscosity and haematocrit content.

OBJECT OF THE INVENTION

It is an object of the present invention to provide a method of analysis and apparatus for use in the method which avoid or ameliorate at least some of the disadvantages of the prior art. It is an object of preferred forms of the invention to provide a biosensor of improved accuracy, and/or reliability and/or speed and a method for its use.

DISCLOSURE OF THE INVENTION

According to one aspect the invention consists in a method for determining the concentration of a reduced (or oxidised) form of a redox species in an electrochemical cell of the kind comprising a working electrode and a counter electrode spaced from the working electrode by a predetermined distance, said method comprising the steps of:

(1) applying an electric potential difference between the electrodes, (2) selecting the potential of the working electrode such that the rate of electro-oxidation of the reduced form (or electro-reduction of the oxidised form) of the species is diffusion controlled, (3) selecting the spacing between the working electrode and the counter electrode so that reaction products from the counter electrode arrive at the working electrode, (4) determining current as a function of time after application of the potential and prior to achievement of a steady state, (5) estimating the magnitude of the steady state current, and (6) obtaining from the change in current with time and the magnitude of the steady state current, a value indicative of the diffusion coefficient and/or of the concentration of the reduced form (or the oxidised form) of the species.

The concentration measured in this way is substantially independent of variation if any in the diffusion coefficient of the reduced form, and therefore is compensated for variations in temperature and viscosity. The concentration so measured is independent of variations in haematocrit and other substances which affect the diffusion coefficient of the reduced form of the redox species.

It will be appreciated that the method of the invention is equally applicable for determining the concentration of a reduced form of a redox species or an oxidized form of a redox species in the cell. In the case that the concentration of the reduced form is to be determined the potential of the working electrode must be maintained such that the rate of electro oxidation of the reduced form is diffusion controlled in step (2) and it is the concentration of the reduced form that is obtained in step (5). In the case that the concentration of oxidized form is to be determined, the potential of the working electrode must be maintained such that the rate of electro reduction of the oxidized form is diffusion controlled in step (2) and it is the concentration of the oxidized form that is obtained in step (5).

The redox species may be an analyte or may be a redox mediator.

In preferred embodiments of the method a mediator is used and the concentration of the reduced (or oxidized) form of the mediator is in turn indicative of the concentration of an analyte,and a measure of the diffusion coefficient of the reduced (or oxidized) form of the mediator is determined as a precursor to the determination of the concentration of the analyte.

For preference the cell comprises a working electrode and counter/reference electrode. If a reference electrode separate from a counter electrode is used, then the reference electrode may be in any convenient location in which it is in contact with the sample in the sensor.

In contrast to prior art, when conducting the method of the invention, the electrodes are sufficiently close that the products of electrochemical reaction at the counter electrode migrate to the working electrode during the period of the test. For example, in an enzyme ferricyanide system, the ferrocyanide produced at the counter electrode diffuses to the working electrode.

This allows a steady state concentration profile to be achieved between the electrodes leading to a steady state current. This in turn allows the diffusion coefficient and concentration of the redox species (mediator) to be measured independently of sample variations and therefore greatly improves accuracy and reliability.

The method also permits the haematocrit concentration of blood to be determined from the diffusion coefficient by use of look-up tables (or by separation of red cells from plasma and measurement of the diffusion coefficient of the red cell fraction) and the plasma fraction, and comparing the two.

According to a second aspect, the invention consists in apparatus for determining the concentration of a redox species in an electrochemical cell comprising:

an electrochemical cell having a working electrode and a counter (or counter/reference) electrode, means for applying an electric potential difference between said electrodes, means for measuring the change in current with time, and characterised in that the working electrode is spaced from the counter electrode by less than 500 μm.

In preferred embodiments the cell has an effective volume of 1.5 microlitres less. Apparatus for use in the invention may comprise a porous membrane, a working electrode on one side of the membrane, a counter/reference electrode on the other side, said electrodes together with a zone of the membrane therebetween defining an electrochemical cell, and wherein the membrane extends laterally from the cell to a sample deposition area spaced apart from the cell zone by a distance greater than the thickness of the membrane.

Preferably the porous membrane, the distance of the target area from the cell portion, and the membrane thickness are so selected in combination that when blood (comprising plasma and red cells) is placed on the target area a plasma front diffuses laterally towards the electrochemical cell zone in advance of the red cells.

It is thus possible to fill a thin layer electrochemical cell with plasma substantially free of haematocrit which would cause a variation in the diffusion coefficient of the redox mediator and which would affect the accuracy of the test as hereinafter explained.

In preferred embodiments of the biosensor according to the invention a second electrochemical cell zone of the membrane is defined by a second working electrode and a second counter/reference electrode on the opposite side of the membrane from the second working electrode. The second electrochemical cell zone is situated intermediate the first cell zone and the sample deposition or "target" area, or is situated on the side of the target area remote from the first electrochemical zone. In these embodiments the plasma comes into contact with enzyme in or on route to, the first electrochemical cell while plasma reaching the second cell does not. The first cell thus in use measures the concentration of reduced mediator in the presence of plasma (including electrochemically interfering substances), and enzyme while the second electrochemical cell measures it in the presence of plasma (including electrochemically interfering substances) and in the absence of enzyme. This allows determination of the concentration of the reduced interfering substances in the second cell and the concentration of reduced interfering substances plus analyte in the first cell. Subtraction of the one value from the other gives the absolute concentration of analyte.

In a highly preferred embodiment of the invention a hollow cell is employed wherein the working and reference (or counter/reference) electrodes are spaced apart by less than 500 μm and preferably by from 20-200 μm.

DESCRIPTION OF THE DRAWINGS

The invention will now be more particularly described by way of example only with reference to the accompanying drawings wherein:

In FIGS. 5 to 12, components corresponding in function to components of the embodiment of FIGS. 1 to 4 are identified by identical numerals or indicia.

DESCRIPTION OF PREFERRED EMBODIMENTS

Figure 1:
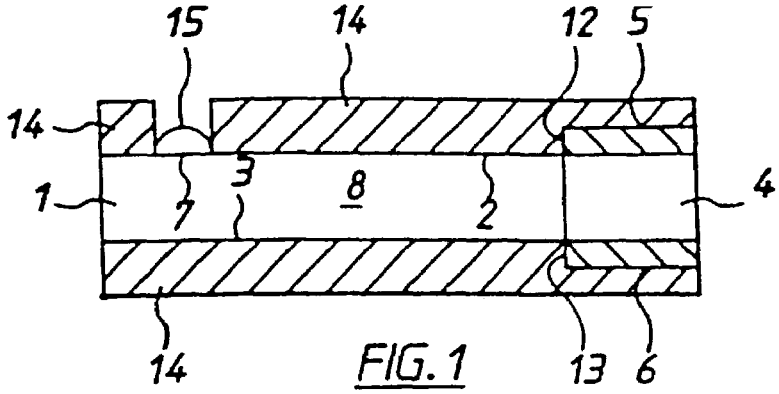
FIG. 1 is a schematic drawing (not to scale) of a first embodiment according to the invention shown in side elevation.
Figure 2:
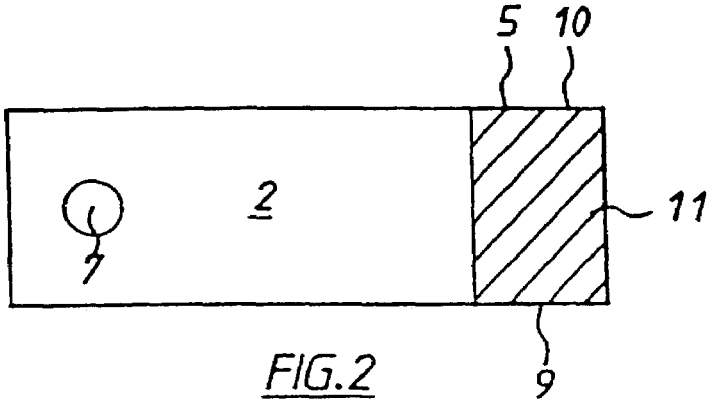
FIG. 2 shows the embodiment of FIG. 1 in plan, viewed from above.
Figure 3:
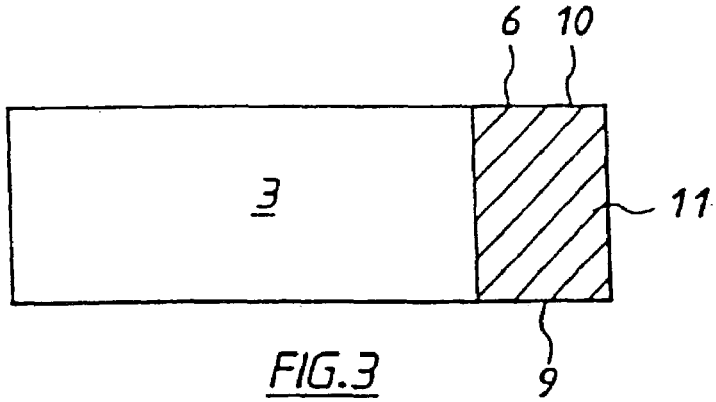
FIG. 3 shows the embodiment of FIG. 1 in plan, viewed from below.
Figure 4:
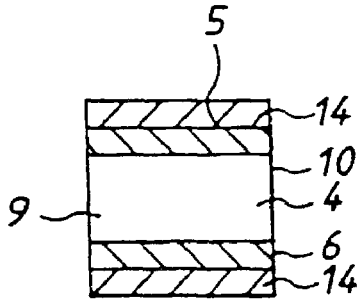
FIG. 4 shows the embodiment of FIG. 1 viewed in end elevation.

With reference to FIGS. 1 to 4 there is shown a first embodiment of apparatus of the invention, in this case a biosensor for determining glucose in blood. The embodiment comprises a thin strip membrane 1 having upper and lower surfaces 2, 3 and having a cell zone 4 defined between a working electrode 5 disposed on upper surface 2 and a counter electrode 6 disposed on lower surface 3. The membrane thickness is selected so that the electrodes are separated by a distance "1" which is sufficiently close that the products of electrochemical reaction at the counter electrode migrate to the working electrode during the time of the test and a steady state diffusion profile is substantially achieved. Typically, "1" will be less than 500 μm. A sample deposition or "target" area 7 defined on upper surface 2 of membrane 1 is spaced at a distance greater than the membrane thickness from cell zone 4. Membrane 1 has a diffusion zone 8 extending between target area 7 and cell zone 4. A suitable reagent including a redox mediator "M", an enzyme "E" and a pH buffer "B" are contained within cell zone 4 of the membrane and/or between cell zone 4 and target area 7. The reagent may also include stabilisers and the like.

In some cases it is preferable to locate the enzyme and mediator and/or the buffer in different zones of the membrane. For example the mediator may be initially located within electrochemical cell zone 4 while the enzyme may be situated below target area 7 or in diffusion zone 8.

Haemoglobin releases oxygen at low pH's, but at higher pH's it binds oxygen very firmly. Oxygen acts as a redox mediator for glucose oxidase dehydrogenase (GOD). In a glucose sensor this competes with the redox mediator leading to low estimates of glucose concentration. Therefore if desired a first pH buffer can be contained in the vicinity of target area 7 to raise the pH to such a level that all the oxygen is bound to haemoglobin. Such a pH would be non-optimal for GOD/glucose kinetics and would consequently be detrimental to the speed and sensitivity of the test. In a preferred embodiment of the invention a second pH buffer is contained as a reagent in the vicinity of the working electrode to restore the pH to kinetically optimal levels. The use of a second buffer does not cause oxygen to be released from the haemoglobin as the haemoglobin is contained within the blood cells which are retained near blood target area 7 or are retarded in diffusion in comparison with the plasma and therefore not influenced by the second buffer. In this manner oxygen interference may be greatly reduced or eliminated.

In use of the sensor a drop of blood containing a concentration of glucose to be determined is placed on target zone 7. The blood components wick towards cell zone 4, the plasma component diffusing more rapidly than red blood cells so that a plasma front reaches cell zone 4 in advance of blood cells.

When the plasma wicks into contact with the reagent, the reagent is dissolved and a reaction occurs that oxidises the analyte and reduces the mediator. After allowing a predetermined time to complete this reaction an electric potential difference is applied between the working electrode and the counter electrode. The potential of the working electrode is kept sufficiently anodic such that the rate of electro oxidation of the reduced form of the mediator at the working electrode is determined by the rate of diffusion of the reduced form of the mediator to the working electrode, and not by the rate of electron transfer across the electrode/solution interface.

In addition the concentration of the oxidised form of the mediator at the counter electrode is maintained at a level sufficient to ensure that when a current flows in the electrochemical cell the potential of the counter electrode, and thus also the potential of the working electrode, is not shifted so far in the cathodic direction that the potential of the working electrode is no longer in the diffusion controlled region. That is to say, the concentration of the oxidized form at the counter electrode must be sufficient to maintain diffusion controlled electro oxidation of the reduced form of the mediator at the working electrode.

The behaviour of a thin layer cell is such that if both oxidised and reduced forms of the redox couple are present, eventually a steady state concentration profile is established across the cell. This results in a steady state current. It has been found that by comparing a measure of the steady state current with the rate at which the current varies in the current transient before the steady state is achieved, the diffusion coefficient of the redox mediator can be measured as well as its concentration. This is in contrast to the Cottrell current that is measured in the prior art. By measuring the Cottrell current at known times after application of a potential to the sensor electrodes it is only possible to determine the product concentration times square root of the diffusion coefficient and therefore it is not possible to determine the concentration of the mediator independent of its diffusion coefficient.

In a cell according to the current invention, by solving the appropriate diffusion equations it can be shown that over a restricted time range a plot of $\ln(i/i^{\infty}-1)$ vs time (measured in seconds) is linear and has a slope (denoted by S) which is equal to $-4\pi^2D/l^2$, where "i" is the current at time "t", "$i^{\infty}$" is the steady state current, "D" is the diffusion coefficient in $cm^2/sec$, "1" is the distance between the electrodes in cm and "π" is approximately 3.14159. The concentration of reduced mediator present when the potential was applied between the electrodes is given by $2\pi^2 i^{\infty}/FA1S$, where "F" is Faraday's constant, A is the working electrode area and the other symbols are as given above. As this later formula uses S it includes the measured value of the diffusion coefficient.

Since 1 is a constant for a given cell, measurement of i as a function of time and $i^{\infty}$ enable the value of the diffusion coefficient of the redox mediator to be calculated and the concentration of the analyte to be determined.

Moreover the determination of analyte concentration compensates for any variation to the diffusion coefficient of the species which is electro oxidised or electro reduced at the working electrode. Changes in the value of the diffusion coefficient may occur as a result of changes in the temperature and viscosity of the solution or variation of the membrane permeability. Other adjustments to the measured value of the concentration may be necessary to account for other factors such as changes to the cell geometry, changes to the enzyme chemistry or other factors which may effect the measured concentration. If the measurement is made on plasma substantially free of haematocrit (which if present causes variation in the diffusion coefficient of the redox mediator) the accuracy of the method is further improved.

Each of electrodes 5, 6 has a predefined area In the embodiments of FIGS. 1 to 4 cell zone 4 is defined by edges 9, 10, 11 of the membrane which correspond with edges of electrodes 5, 6 and by leading (with respect to target area 7) edges 12, 13 of the electrodes. In the present example the electrodes are about 600 angstrom thick and are from 1 to 5 mm wide.

Optionally, both sides of the membrane are covered with the exception of the target area 7 by laminating layers 14 (omitted from plan views) which serves to prevent evaporation of water from the sample and to provide mechanical robustness to the apparatus. Evaporation of water is undesirable as it concentrates the sample, allows the electrodes to dry out, and allows the solution to cool, affecting the diffusion coefficient and slowing the enzyme kinetics, although diffusion coefficient can be estimated as above.

Figure 5:
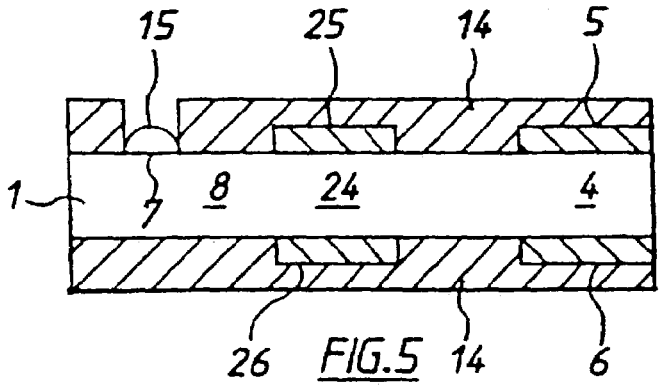
FIG. 5 is a schematic drawing (not to scale) of a second embodiment according to the invention in side elevation.
Figure 6:
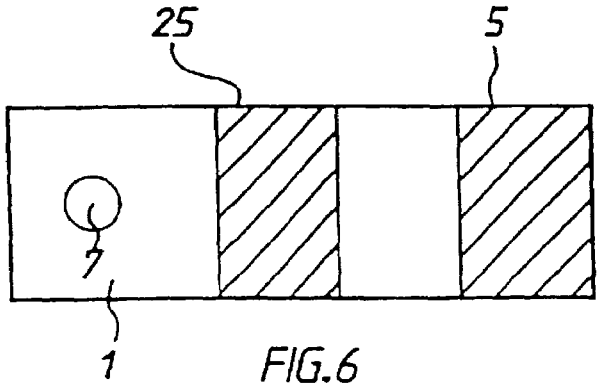
FIG. 6 shows the embodiment of FIG. 5 in plan, viewed from above.

A second embodiment according to the invention, shown in FIGS. 5 and 6, differs, from the first embodiment by inclusion of a second working electrode 25 and counter/reference electrode 26 defining a second cell zone 24 therebetween. These electrodes are also spaced apart by less than 500 μm in the present example. Second electrodes 25, 26 are situated intermediate cell zone 4 and target area 7. In this embodiment the redox mediator is contained in the membrane below or adjacent to target area 7 or intermediate target area 7 and first cell zone 4. The enzyme is contained in the membrane in the first cell zone 4 and second cell zone 24. The enzyme does not extend into second cell 24. In this case when blood is added to the target area, it dissolves the redox mediator. This wicks along the membrane so that second electrochemical cell 24 contains redox mediator analyte and serum including electrochemically interfering substances. First electrochemical cell receives mediator, analyte, serum containing electrochemically interfering substances, and enzyme. Potential is now applied between both working electrodes and the counter electrode or electrodes but the change in current with time is measured separately for each pair. This allows the determination of the concentration of reduced mediator in the absence of analyte plus the concentration of electrochemically interfering substances in the second electrochemical cell and the concentration of these plus analyte in the first electrochemical cell. Subtraction of the one value from the other gives the absolute concentration of analyte.

Figure 7:
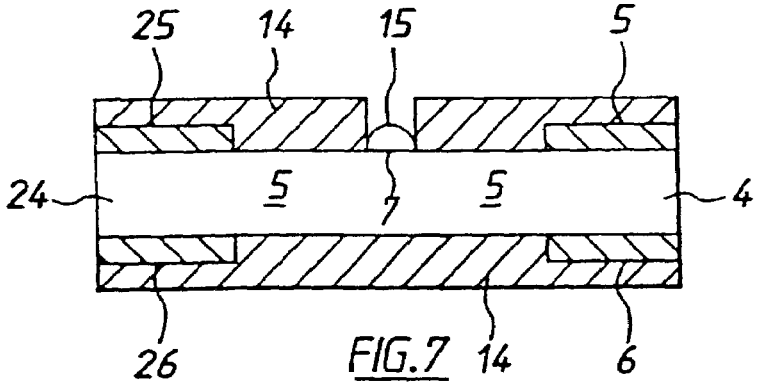
FIG. 7 is a schematic drawing (not to scale) of a third embodiment according to the invention, in side elevation.
Figure 8:
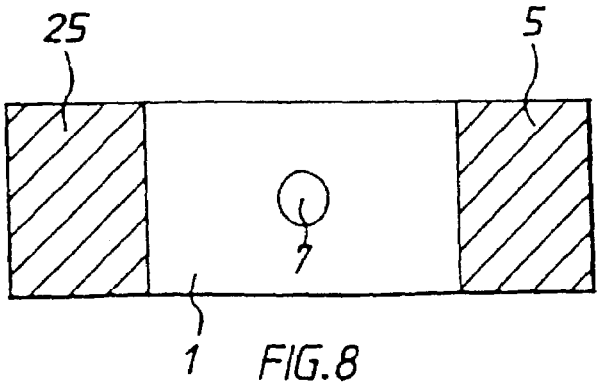
FIG. 8 shows the embodiment of FIG. 7 in plan, viewed from above.

The same benefit is achieved by a different geometry in the embodiment of FIGS. 7 and 8 in which the second working electrode and second counter/reference electrode define the second cell 24 on the side of target area 7 remote from first electrochemical cell 4. In this case the enzyme may be contained in the membrane strip between the target area and cell 1. The redox mediator may be in the vicinity of the target area or between the target area and each cell. The diffusion coefficient of mediator is lowered by undissolved enzyme and the arrangement of FIGS. 7 and 8 has the advantage of keeping enzyme out of the thin layer cells and allowing a faster test (as the steady state current is reached more quickly). Furthermore the diffusion constant of redox mediator is then the same in both thin layer cells allowing more accurate subtraction of interference.

Figure 9:
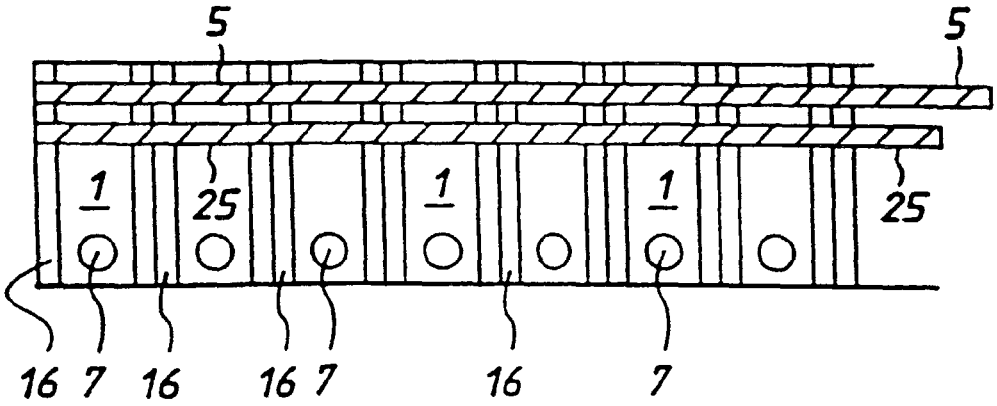
FIG. 9 is a schematic drawing (not to scale) according to the invention in plan view, viewed from above.
Figure 10:
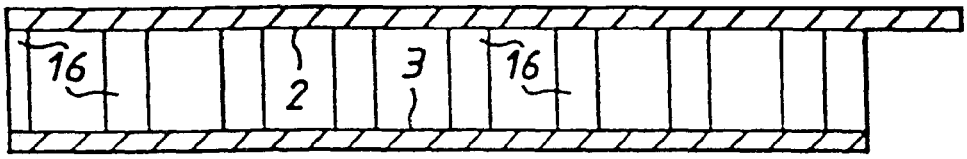
FIG. 10 shows the embodiment of FIG. 9 in end elevation.
Figure 11:
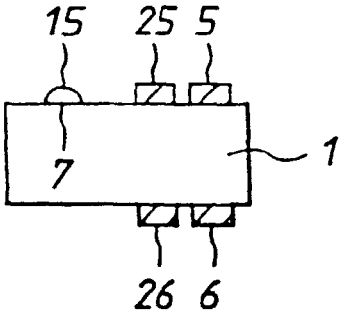
FIG. 11 shows the embodiment of FIG. 9 in side elevation.

Although the embodiments of FIGS. 1 to 8 are unitary sensors, it will be understood that a plurality of sensors may be formed on a single membrane as shown in the embodiment of FIGS. 9 to 11. In this case the electrodes of one sensor are conductively connected to those of an adjacent sensor. Sensors may be used successively and severed from the strip after use.

In the embodiment of FIGS. 9 to 11 electrode dimensions are defined in the diffusion direction (indicated by arrow) by the width of the electrode in that direction. The effective dimension of the electrode in a direction transverse to diffusion direction is defined between compressed volumes 16 of the membrane in a manner more fully described in co-pending Application PCT/AU96/00210, the disclosure of which is incorporated herein by reference in its entirety. For clarity optional laminated layer 14 of FIG. 1 has been omitted from FIGS. 9 to 11.

Figure 12:
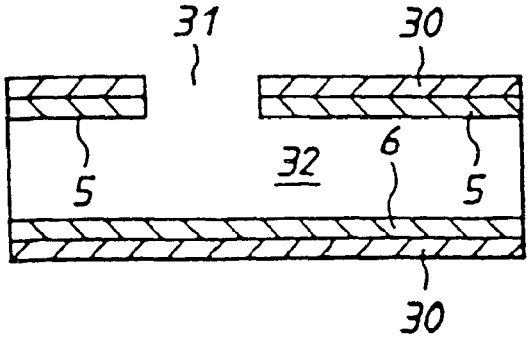
FIG. 12 shows a schematic drawing (not to scale) of a hollow cell embodiment according to the invention, viewed in cross section.

In the embodiment of FIG. 12 there is shown a hollow cell according to the invention wherein the electrodes 5, 6 are supported by spaced apart polymer walls 30 to define a hollow cell. An opening 31 is provided on one side of the cell whereby a sample can be admitted into cavity 32. In this embodiment a membrane is not used. As in previous embodiments, the electrodes are spaced apart by less than 500 μm, preferably 20-400 μm and more preferably 20-200 μm. Desirably the effective cell volume is 1.5 microlitres or less.

It will be understood that the method of the invention may be performed with a cell constructed in accord with co-pending application PCT/AU95/00207 or cells of other known design, provided these are modified to provide a sufficiently small distance between electrode faces.

Figure 13:
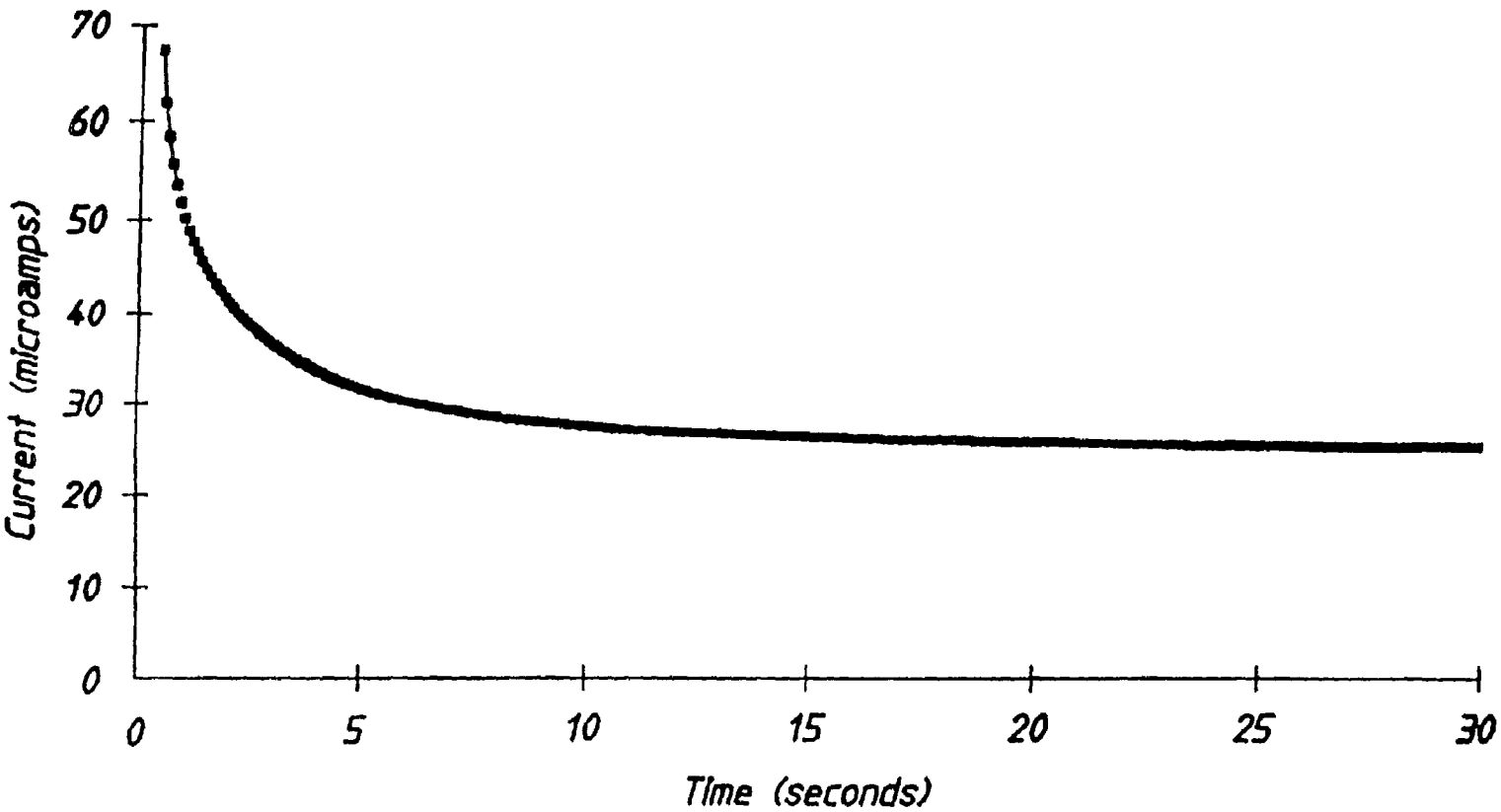
FIG. 13 is a graph showing a plot of current (ordinate axis) versus time (co-ordinate axis) during conduct of a method according to the invention.
Figure 14:
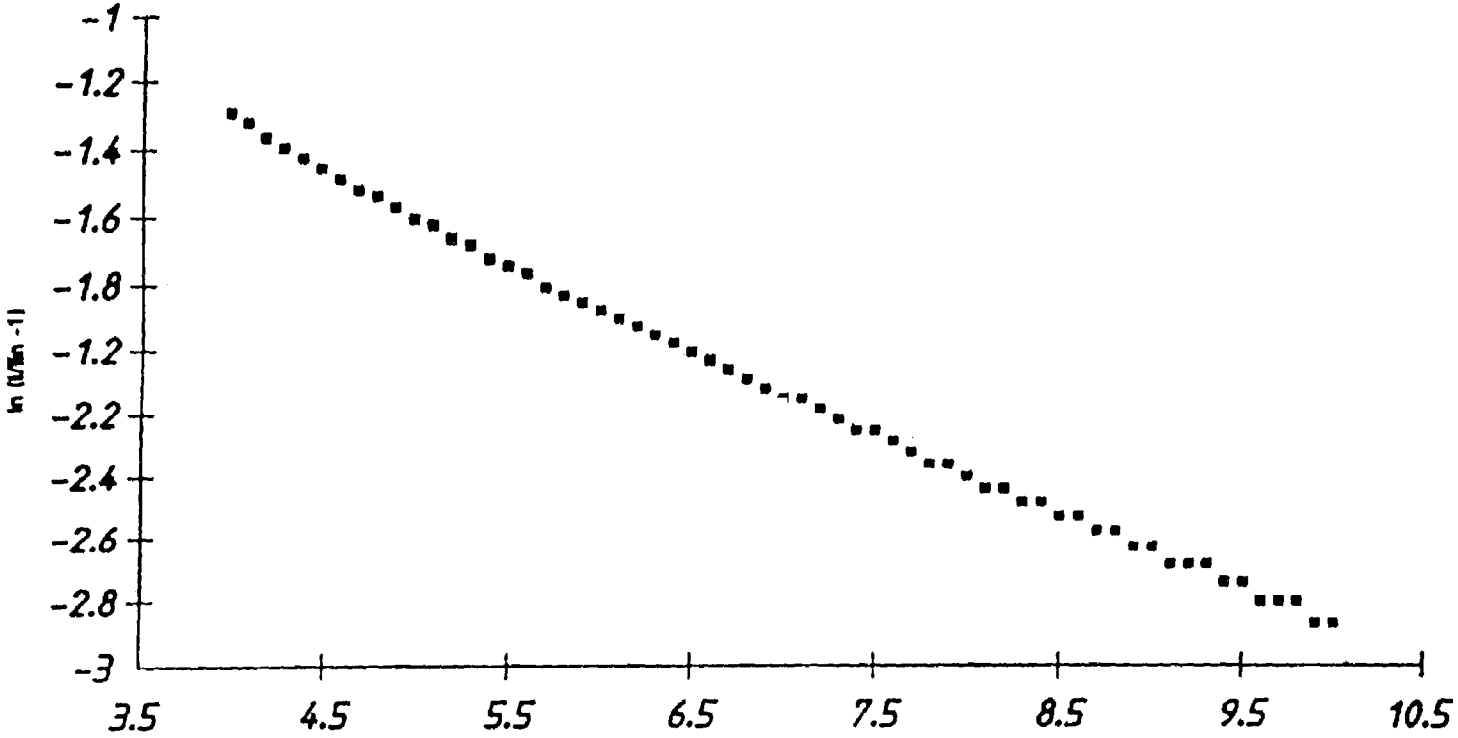
FIG. 14 is a further graph of use in explaining the method of the invention.

The method of the invention will now be further exemplified with reference to FIGS. 13 and 14.

EXAMPLE 1

A membrane 130 microns thick was coated on both sides with a layer of Platinum 60 nanometers thick. An area of 12.6 sq. mm was defined by compressing the membrane. 1.5 microlitres of a solution containing 0.2 Molar potassium ferricyanide and 1% by weight glucose oxidase dehydrogenase was added to the defined area of the membrane and the water allowed to evaporate.

The platinum layers were then connected to a potentiostat to be used as the working and counter/reference electrodes. 3.0 microlitres of an aqueous solution containing 5 millimolar D-glucose and 0.9 wt % NaCl was dropped on to the defined area of the membrane. After an elapse of 20 seconds a voltage of 300 millivolts was applied between the working and counter/reference electrodes and the current recorded for a further 30 seconds at intervals of 0.1 seconds.

FIG. 13 is a graph of current versus time based on the above measurements. Using a value of the steady state current of 26.9 microamps the function ln(i/26.9−1) was computed and plotted versus time. The slope of the graph (FIG. 14) is −0.342 which corresponds to a diffusion coefficient of $1.5\times10^{-6}$ $cm^2$ per second and a corrected glucose concentration (subtracting background ferrocyanide) of 5.0 millimolar.

The steady state current is one in which no further significant current change occurs during the test. As will be understood by those skilled in the art, a minimum current may be reached after which there may be a drift due to factors such as lateral diffusion, evaporation, interfering electrochemical reactions or the like. However, in practice it is not difficult to estimate the "steady state" current ($i^{\infty}$). One method for doing so involves approximating an initial value for $i^{\infty}$. Using the fit of the i versus t data to the theoretical curve a better estimate of $i^{\infty}$ is then obtained. This is repeated reiteratively until the mewed value and approximated value converge to within an acceptable difference, thus yielding an estimated $i^{\infty}$.

In practice, the measurements of current i at time t are made between a minimum time t min and a maximum time t max after the potential is applied. The minimum and maximum time are determined by the applicability of the equations and can readily be determined by experiment of a routine nature. If desired the test may be repeated by switching off the voltage and allowing the concentration profiles of the redox species to return towards their initial states.

It is to be understood that the analysis of the current v. time curve to obtain values of the Diffusion Co-efficient and/or concentration is not limited to the method given above but could also be achieved by other methods.

For instance, the early part of the current v. time curve could be analysed by the Cottrell equation to obtain a value of $D^{1/2}\times Co$ (Co=Concentration of analyte) and the steady state current analysed to obtain a value of D×Co. These 2 values can then be compared to obtain D and C separately.

It will be understood that in practice of the invention an electrical signal is issued by the apparatus which is indicative of change in current with time. The signal may be an analogue or digital signal or may be a series of signals issued at predetermined time intervals. These signals may be processed by means of a microprocessor or other conventional circuit to perform the required calculations in accordance with stored algorithms to yield an output signal indicative of the diffusion coefficient, analyte concentration, haematocrit concentration or the like respectively. One or more such output signals may be displayed by means of an analogue or digital display.

It is also possible by suitable cell design to operate the cell as a depletion cell measuring the current required to deplete the mediator. For example in the embodiment of FIG. 5 the method of the invention may be performed using electrodes 5, 6, which are spaced apart by less than 500 μm. An amperometric or voltametric depletion measurement may be made using electrodes 5 and 26 which are spaced apart more than 500 μm and such that there is no interference between the redox species being amperometrically determined at electrodes 5, 26.

The depletion measurement may be made prior to, during or subsequent to, the measurement of diffusion coefficient by the method of the invention. This enables a substantial improvement in accuracy and reproducibility to be obtained.

In the embodiments described the membrane is preferably an asymmetric porous membrane of the kind described in U.S. Pat. Nos. 4,629,563 and 4,774,039 both of which are incorporated herein in their entirety by reference. However symmetrical porous membranes may the employed. The membrane may be in the form of a sheet, tube, hollow fibre or other suitable form.

If the membrane is symmetric the target area is preferably on the more open side of the asymmetric membrane. The uncompressed membrane desirably has a thickness of from 20 to 500 μm. The minimum thickness is selected having regard to speed, sensitivity, accuracy and cost. If desired a gel may be employed to separate haematocrit from GOD. The gel may be present between the electrodes and/or in the space between the sample application area and the electrodes.

The working electrode is of any suitable metal for example gold, silver, platinum, palladium, iridium, lead, a suitable alloy. The working electrode may be preformed or formed in situ by any suitable method for example sputtering, evaporation under partial vacuum, by electrodeless plating, electroplating, or the like. Suitable non-metal conductors may also be used for electrode construction. For example, conducting polymers such as poly(pyrrole), poly(aniline), porphyrin "wires" poly(isoprene) and poly (cis-butadiene) doped with iodine and "ladder polymers". Other non-metal electrodes may be graphite or carbon mixed with a binder, or a carbon filled plastic. Inorganic electrodes such as $In_2O_3$ or $SnO_2$ may also be used. The counter/reference electrode may for example be of similar construction to the working electrode. Nickel hydroxide or a silver halide may also be used to form the counter/reference electrode. Silver chloride may be employed but it will be understood that chloridisation may not be necessary and silver may be used if sufficient chloride ions are present in the blood sample. Although in the embodiments described the working electrode is shown on the upper surface of the biosensor and the counter/reference electrode is on the lower surface, these may be reversed.

It is preferable that the working electrode and counter (or counter/reference) electrodes are of substantially the same effective geometric area.

If a separate reference and counter electrode are employed, they may be of similar construction. The reference electrode can be in any suitable location.

It will be understood that the features of one embodiment hereindescribed may be combined with those of another. The invention is not limited to use with any particular combination of enzyme and mediator and combinations such as are described in EP 0351892 or elsewhere may be employed. The system may be used to determine analytes other than glucose (for example, cholesterol) by suitable adaptation of reagents and by appropriate membrane selection. The system may also be adapted for use with media other than blood. For example the method may be employed to determine the concentration of contaminants such as chlorine, iron, lead, cadmium, copper, etc., in water.

Although the cells herein described have generally planar and parallel electrodes it will be understood that other configurations may be employed, for example one electrode could be a rod or needle and the other a concentric sleeve.

It will be apparent to those skilled in the art from the disclosure hereof the invention may be embodied in other forms without departing from the inventive concept herein disclosed.

What is claimed is:

1. An [electrochemical biosensor] *apparatus* comprising:

(1) a hollow electrochemical cell for measuring a concentration of glucose in a blood sample, the hollow electrochemical cell comprising:

(a) at least one non-metal working electrode;

(b) at least one counter electrode or counter/reference electrode, wherein the working electrode and the counter electrode or counter/reference electrode face each other, are located on different planes, and are separated by a distance of from about 20 microns to about 200 microns;

(c) a spacer interposed between the working electrode and the counter electrode or counter/reference electrode, wherein the spacer comprises a non-conductive polymeric material, and wherein the hollow electrochemical cell has an effective cell volume of less than 1.5 microliters; and (2) circuitry configured to determine the diffusion coefficient of a redox mediator in the cell, and independently its concentration, from cell current.

2. The [electrochemical biosensor] *apparatus* of claim 1, wherein at least one non-metal working electrode comprises a material selected from the group consisting of graphite, carbon, and carbon-filled plastic.

3. The [electrochemical biosensor] *apparatus* of claim 2, wherein at least one counter electrode or counter/reference electrode comprises a metal substrate or a metal coated substrate.

4. The [electrochemical biosensor] *apparatus* of claim 3, wherein the metal is selected from the group consisting of gold, silver, platinum, palladium, iridium, lead, and alloys thereof.

5. The [electrochemical biosensor] *apparatus* of claim 4, wherein the metal comprises silver, and wherein the blood sample comprises chloride ions and a reduced form of a redox species or an oxidized form of a redox species.

6. The [electrochemical biosensor] *apparatus* of claim 1, wherein walls of the spacer and the electrodes define the effective cell volume of the hollow electrochemical cell.

7. The [electrochemical biosensor] *apparatus* of claim 1, wherein the circuitry comprises a microprocessor.

8. The [electrochemical biosensor] *apparatus* of claim 1, wherein the working electrode and the counter electrode or counter/reference electrode are planar electrodes.

9. The [electrochemical biosensor] *apparatus* of claim 1, wherein the circuitry is configured to achieve a steady-state current.

10. The [electrochemical biosensor] *apparatus* of claim 1, wherein the at least one counter electrode or counter/reference electrode is only a single electrode.

11. The [electrochemical biosensor] *apparatus* of claim 1, wherein the circuitry is configured to maintain an approximately fixed potential to determine the diffusion coefficient and concentration of the redox mediator.

* * * * *